United States Patent [19]

Grandjean et al.

[11] Patent Number: 5,009,229
[45] Date of Patent: Apr. 23, 1991

[54] STEROID ELUTING INTRAMUSCULAR LEAD

[75] Inventors: Pierre-Andre Grandjean, Bassenge, Belgium; Philip H. J. Lee, Woodbury, Minn.

[73] Assignee: Medtronic, Inc., Minneapolis, Minn.

[21] Appl. No.: 446,594

[22] Filed: Dec. 6, 1989

[51] Int. Cl.$^5$ .............................................. A61N 1/05
[52] U.S. Cl. ................................. 128/419 P; 128/785
[58] Field of Search ................... 128/419 P, 784, 785, 128/786; 606/228, 229, 320, 331

[56] References Cited

U.S. PATENT DOCUMENTS

| | | | |
|---|---|---|---|
| 3,698,853 | 10/1972 | Wilson | 606/229 |
| 3,896,813 | 7/1975 | Kurtz | 606/229 |
| 3,918,455 | 11/1975 | Coplan | 606/229 |
| 4,338,947 | 7/1982 | Williams | 128/419 P |
| 4,341,226 | 7/1982 | Peters | 128/419 P |
| 4,444,207 | 4/1984 | Robicsek | 128/419 P |
| 4,712,553 | 12/1987 | MacGregor | 623/66 |

Primary Examiner—William E. Kamm
Assistant Examiner—Scott M. Getzow
Attorney, Agent, or Firm—John L. Rooney

[57] ABSTRACT

An improved lead for electrically stimulating muscle tissue particularly configured for a cardiac assist system powered by surgically modified skeletal muscle tissue. The skeletal muscle is either wrapped about the heart itself, or about an auxiliary pumping chamber attached to the aorta. Electrical stimulation is supplied via the improved lead to cause contraction of the skeletal muscle in synchronism with the natural or artificially paced heart rate and timed to obtain the desired hemodynamic effect. The improved lead has an electrode which is embedded in the skeletal muscle. The stimulation threshold of the skeletal muscle is held relatively low by the action of a glucocorticosteroid imbedded within the suture material. By placing the drug material in this position, it acts as an anti-inflammatory along the entire path of the suture material and treats the specific area of the electrode contact from within the muscle itself. The specific area of electrode contact may also be treated from the electrode side by placing a similar drug within the electrode.

6 Claims, 6 Drawing Sheets

STEROID ELUTING INTRAMUSCULAR LEAD

CROSS REFERENCES TO CO-PENDING APPLICATIONS

This application is related to Ser. No. 07/446,593, filed Dec. 6, 1989, entitled "Muscle Fitness Detection by Colorimetry" by the same assignee; Ser. No. 07/446,592, filed Dec. 6, 1989, entitled "Muscle Output Monitor by Intramuscular Temperature Variation Measurement" by the same assignee; and Ser. No. 07/446,811, filed Dec. 6, 1989, entitled "Muscle Contraction Control by Intramuscular Pressure Monitoring" by the same assignee.

BACKGROUND OF THE INVENTION

1. Field of the Invention

The present invention generally pertains to skeletal muscle stimulation, and more particularly, pertains to improved lead systems for stimulating skeletal muscle powered cardiac assist systems.

2. Description of the Prior Art

The use of skeletal muscle tissue to power chronically implantable cardiac assist systems has met with some success. See, for example, U.S. Pat. No. 4,813,952, issued to Aida Khalafalle herein incorporated by reference which describes such a system. Using the patient's own muscle tissue overcomes the problems associated with the storage and transmission of energy from artificial sources. The result is a very compact system requiring no percutaneous energy transmission.

A problem present by the use of skeletal muscle power is application of stimulation signals to cause muscle contraction. The earliest skeletal muscle powered cardiac assist systems used cardiac pacing leads for skeletal muscle stimulation.

A major improvement to such leads is found in the use of steroid eluting pacing leads. U.S. Pat. No. 4,711,251 issued to Stokes, which teaches an endocardial pacing lead having steroid drug embedded in the distal tip. This embedded steroid drug treats the heart tissue immediately in contact with the pacing electrode. U.S. Pat. Nos. 4,506,680; 4,577,642; and 4,606,118 teach similar endocardial leads, all of which treat the electrode contact area with a steroid. U.S. Statutory Invention Registration No. H356 discloses an endocardial pacing lead suitable for epicardial insertion which elutes a steroid drug from the electrode.

All of these pacing leads are directed to stimulating the heart muscle, which is configured in a predetermined shape. The skeletal muscle used to power the cardiac assist system, on the other hand, is likely to be configured in a wide variety of shapes, any specific one of which cannot be known until the surgical procedure is actually performed. For that reason a flexible, specifically designed lead is far more appropriate than one especially directed to cardiac pacing applications.

SUMMARY OF THE INVENTION

The subject invention is an adaptation of a type of cardiac pacing lead (called a heart wire) designed for acute use. The lead has a terminal pin at the proximal end, an insulated wire body, an electrode made by not insulating the distal portion of the conductor, a strand of suture material running the entire length of the lead and extending distal to the electrode, and a curved surgical needle attached to the distal end of the strand of suture material.

In the present invention, the suture material is treated with a steroid drug, such as a glucocorticosteroid, along its entire length. Upon chronic implantation, the steroid drug is eluted from the suture material, thus treating possible tissue inflammation or damage caused by the implantation procedure or subsequent irritation. This treatment is accomplished along the entire length of the suture/tissue contact, not just at the site of the electrode. However, because the suture material runs within the conductor coil, the site of the electrode tissue contact is also treated as in the prior art.

BRIEF DESCRIPTION OF THE DRAWINGS

Other objects of the present invention and many of the attendant advantages of the present invention will be readily appreciated as the same become better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Cardiac assist systems do not replace the patient's natural heart, but merely supplement it in performing blood circulation. This assistance takes two (2) basic forms. The first of these directly assist the natural heart by increasing aortic pressure at the same time as the heart. This may be implemented by wrapping the skeletal muscle about the heart, about the aorta, or about a compressible chamber in series with or parallel to a portion of the aorta.

The second form increases circulatory system pressure during relaxation of the heart. The resulting increase in coronary perfusion provides the desired assistance to the heart by alleviating excess cellular fatigue. With either form of cardiac assist, the heart is electrically sensed to ensure that the skeletal muscle is stimulated in the proper timing relationship to heart contractions.

Figure 1:
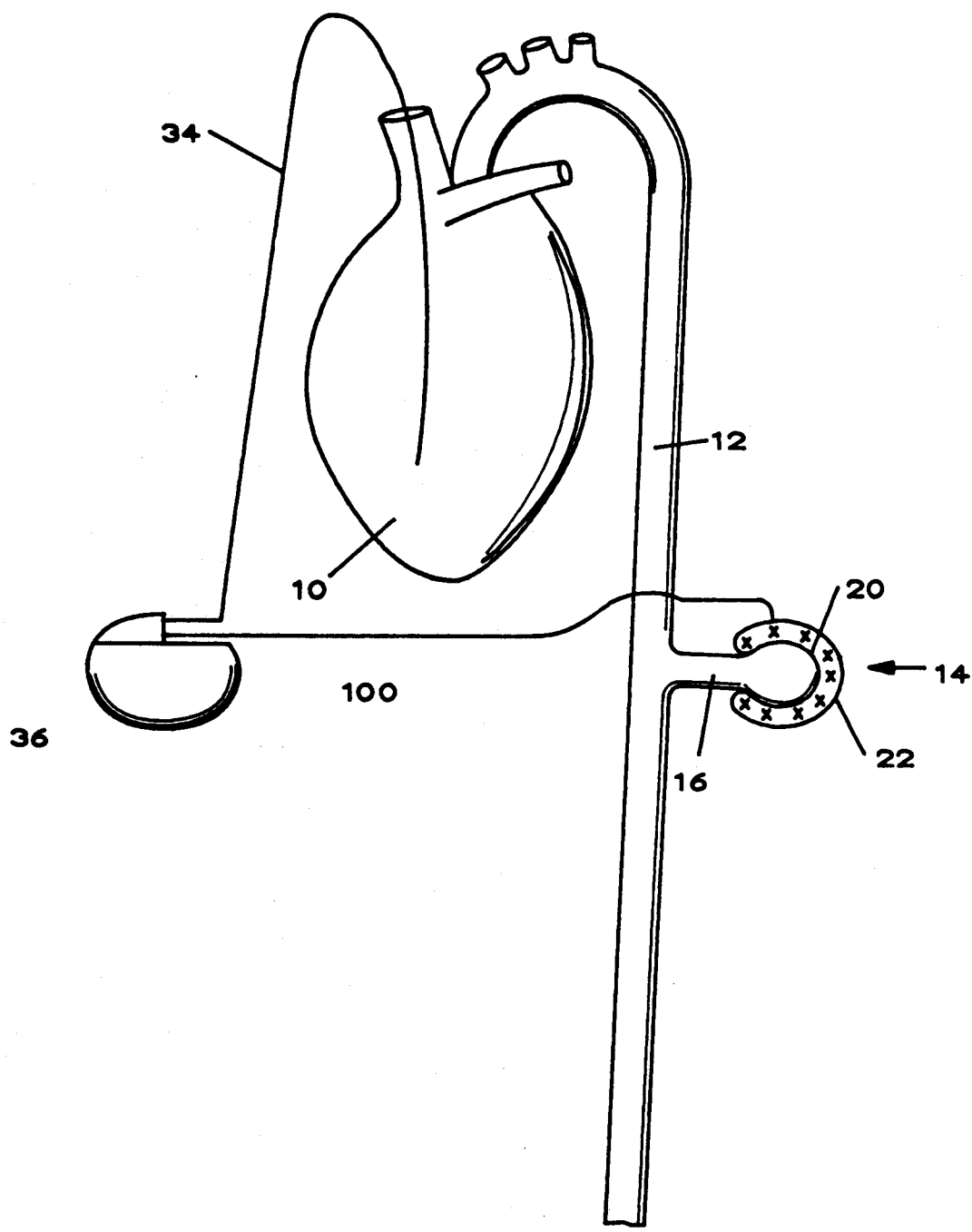
FIG. 1 is an overall view of one configuration of the cardiac assist system.

FIG. 1 shows a typical cardiac assist system. This particular mode performs counter pulsation for enhanced perfusion as an indirect cardiac assist. A single mode is shown for the purpose of illustration only and not by way of limiting the scope of the present invention. Other modes of cardiac assist may be found in U.S. Pat. No. 4,813,952.

Human heart 10 is assisted by counter pulse contraction of skeletal muscle 22 by the enhanced perfusion of cardiac tissue. Pulse generator 36 senses contractions of human heart 10 by tranvenous lead 34. After a delay, phase generator sends stimulating pulses to skeletal muscle 22 via lead 100, thereby inducing contraction.

As skeletal muscle 22 contracts, it reduces the diameter of chamber 20 which is coupled to aorta 12 via stub 16. This contraction increases aortic pressure, thereby improving perfusing through the coronary vascular system.

Skeletal muscle 22 must be conditioned to respond in the desired manner without fatigue. U.S. Pat. No. 4,411,268 issued to James Cox, incorporated herein by reference, teaches such a method of conditioning.

Figure 2:
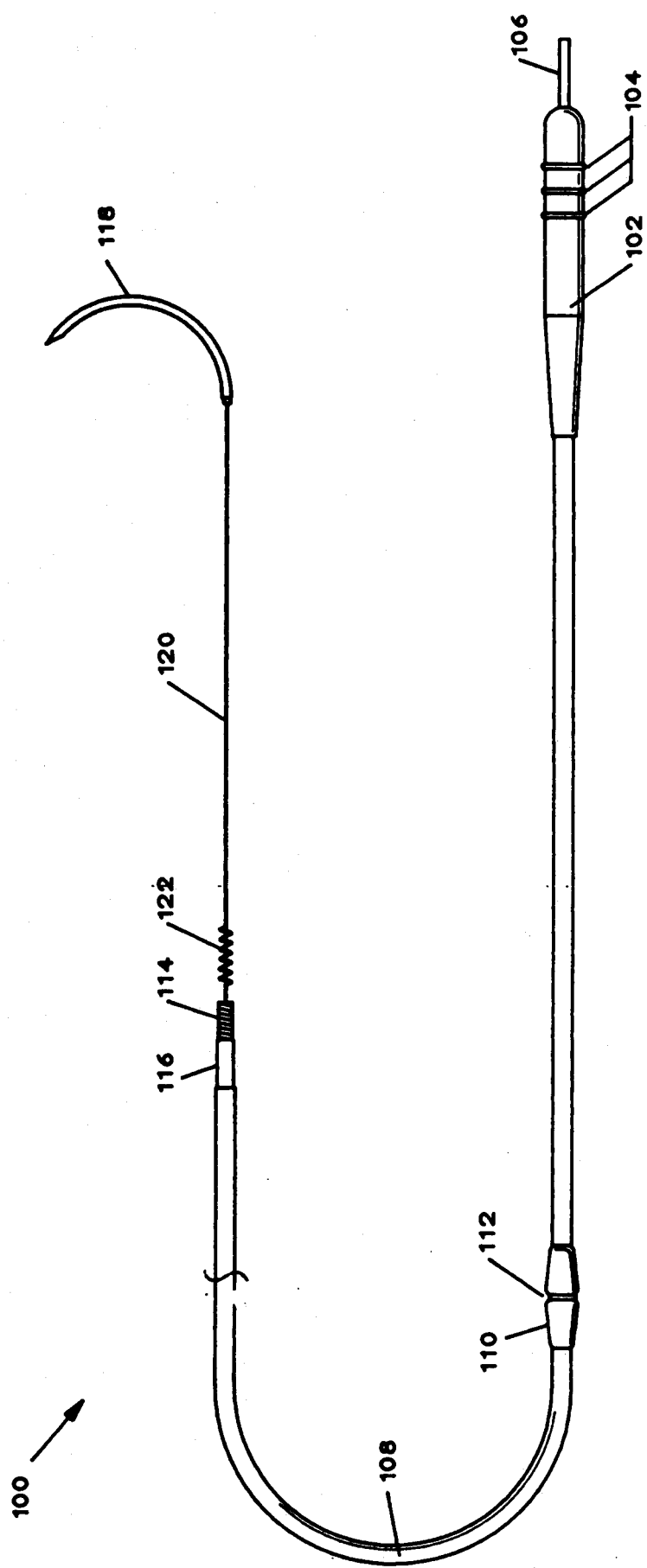
FIG. 2 is a plan view of a chronically implantable stimulation lead of the present invention.

FIG. 2 is a plan view of a chronically implantable lead 100 by stimulation of skeletal muscle which powers the cardiac assist system of FIG. 1. The proximal end of the lead contains a connector 102 which couples to implantable pulse generator 36. Connector 102 has sealing rings 104 which seal the connection with the implantable pulse generator 36 against the ingress of bodily fluids. Terminal pin 106 electrically couples the lead to implantable pulse generator 36.

Insulating sheath 108 insulates lead 100 from unwanted electrical contact with body tissue. Slidable suture sleeve 110 slides along the length of insulating sheath 108. Sutures used to tie down lead 100 are imbedded in groove 112 of slidable suture sleeve 110. Coaxial sheath 116 further helps insulate and strengthen the body of lead 100. Electrode 114 comprises an uninsulated portion of a space wound wire conducting coil internal to insulating sheaths 108 and 116 and coaxial therewith. Electrode 114 is electrically coupled to terminal pin 106.

Strand 120 of suture material of polypropoline or other polymer is mechanically attached to the proximal end of the lead, runs the length of lead 100, and is coaxial with insulating sheaths 108 and 116 and with the conducting coil. A curved surgical needle 118 is mechanically attached to the distal end of strand 120 of suture material. Not easily seen is the steroid drug, preferably a glucocorticosteroid. This drug is releasably imbedded within the polymer of strand 120. During the life of lead 100, this drug leaches out into the surrounding tissue at a predetermined rate.

Preformed helix 122 is deformably molded into strand 120 to aid in attachment. A detailed explanation of preformed helix 122 is found in U.S. Pat. No. 4,341,226 issued to Peters, incorporated herein by reference.

Figure 3:
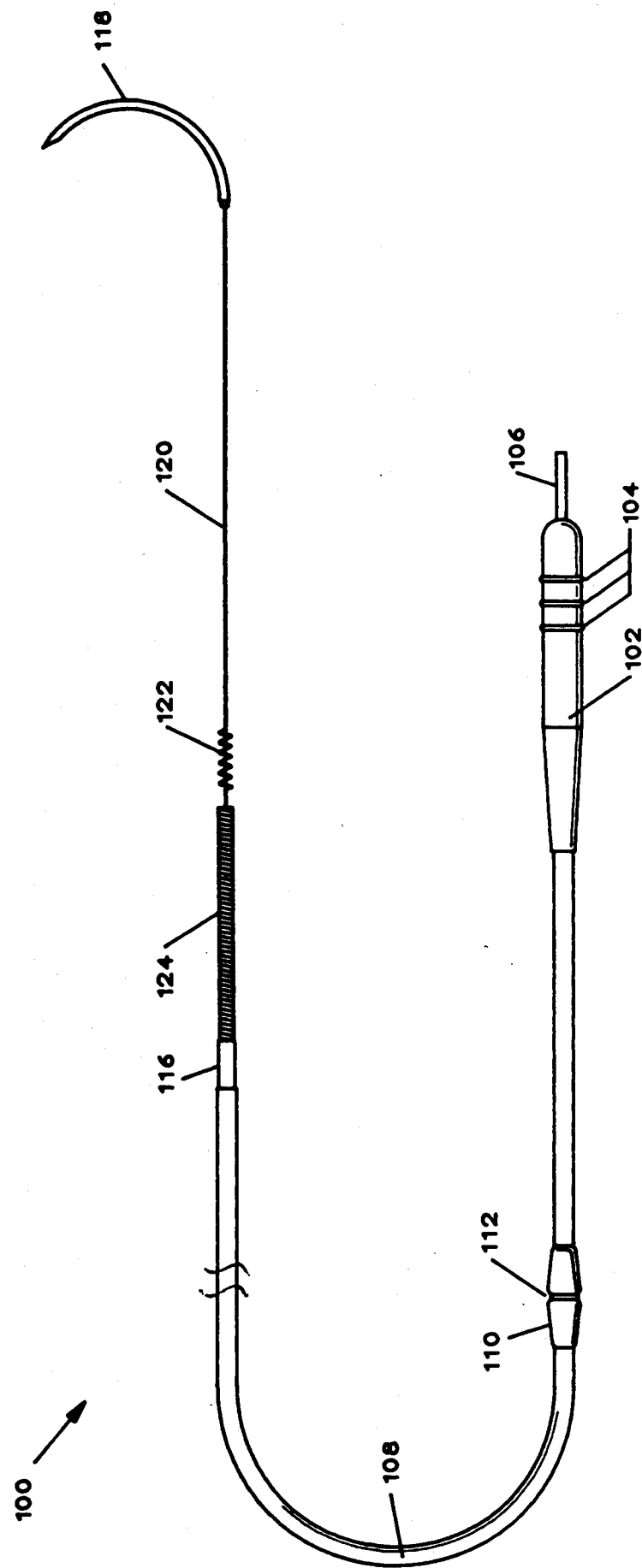
FIG. 3 is a plan view of an alternative embodiment of a chronically implantable stimulation lead of the present invention.

FIG. 3 is an alternative embodiment of the lead of FIG. 2. It is identical in all respects except that electrode 124 replaces electrode 114. Electrode 124 exposes a great deal more of the coiled conductor, thereby creating a much larger surface area for stimulation. The optimal surface area for stimulation varies with the specific application, and will normally be selected by the physician in charge of the surgery.

Figure 4:
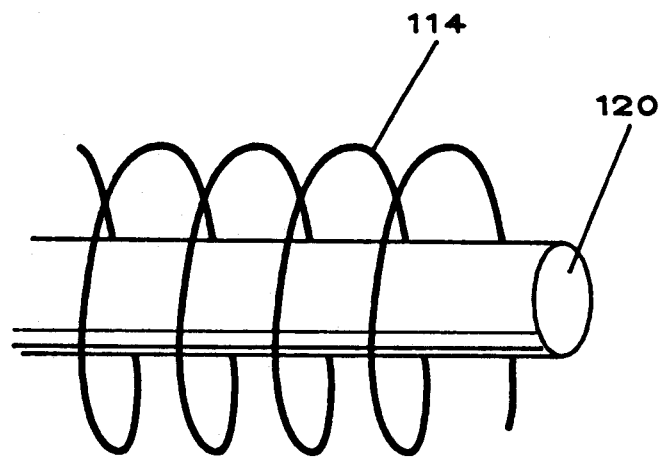
FIG. 4 is a view of the electrode and concentric strand of suture material of the present invention.

FIG. 4 is a close up view of electrode 114 (or electrode 124 in the alternative embodiment) as located concentrically about strand 120 of suture material. As explained above, strand 120 is a polymer imbedded with a glucocorticosteroid.

Figure 5:
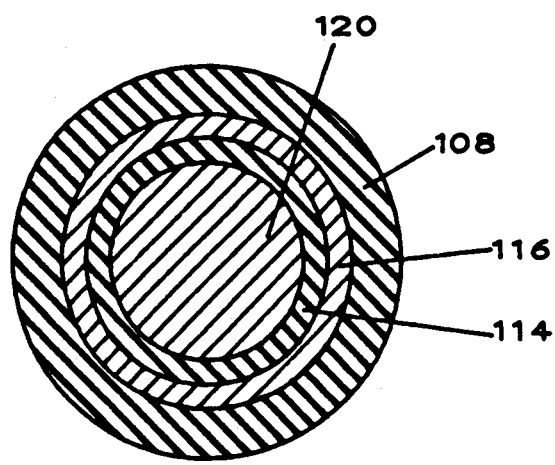
FIG. 5 is a cross-sectional view of the chronically implantable lead.

FIG. 5 is a cross-sectional view of lead 100. Strand 120 comprises the inner diameter. It is surrounded by electrode 114 and insulating sheaths 108 and 116.

Figure 6:
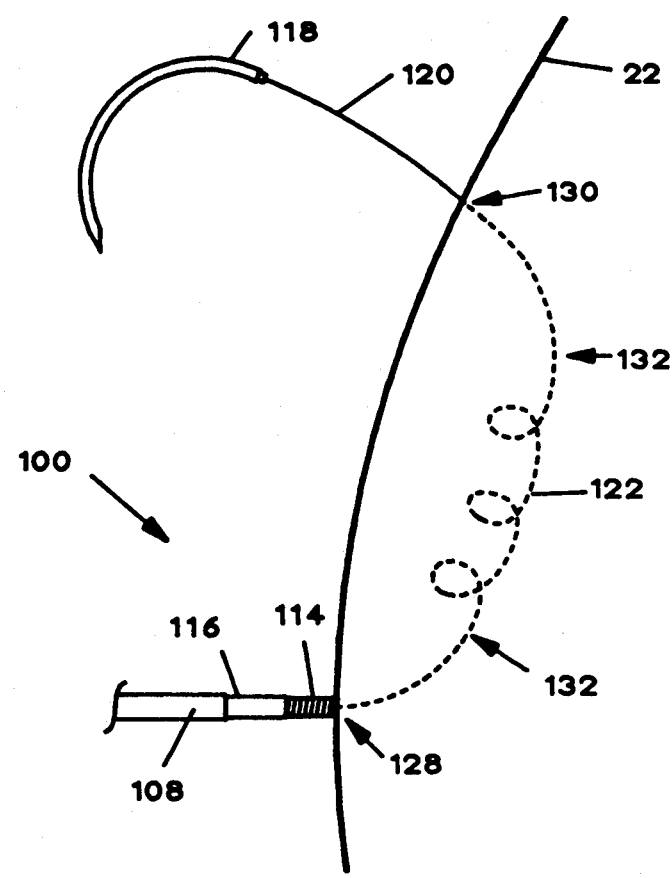
FIG. 6 is a view of the chronically implantable lead as positioned in the skeletal muscle.

FIG. 6 shows the implantation of lead 100. Curved surgical needle 118 enters skeletal muscle 22 at puncture 128. It proceeds along path 132 and exits skeletal muscle 22 at exit point 130. Preformed helix 122 sustains electrode 114 in contact with skeletal muscle 22 at puncture 128. The glucocorticosteroid leaches out from strand 120 all along path 132 including puncture 128 and exit point 130 to minimize acute and chronic irritation.

Having thus described the preferred embodiments, those of skill in the art will be readily able to apply the present invention without departing from the scope of the claims which are hereto attached.

We claim:

1. An apparatus for stimulating a skeletal muscle of a human patient surgically prepared to assist the heart of said human patient comprising:
    a. implantable pulse generator means for generating pulses to stimulate said skeletal muscle in timed relation to said heart of said human patient;
    b. a connector for electrically coupling said pulses from said implantable pulse generator;
    c. at least one sealing ring coupled to said connector to seal said connector to said implantable pulse generator means;
    d. an electrically conducting coil having a proximal end and a distal end wherein said proximal end is electrically coupled to said connector;
    e. an insulating sheath disposed over substantially all of said electrically conducting coil except a portion at said distal end of said electrically conducting coil wherein said portion is sufficient to function as an electrode to couple said pulses to said skeletal muscle;
    f. a length of suture material having a proximal end and a distal end wherein said proximal end is attached to said distal end of said electrically conducting coil;
    g. a suture needle attached to said distal end of said length of suture material;
    h. means coupled to said length of suture material for holding said electrode in contact with said skeletal muscle; and,
    i. means releasably embedded within said length of suture material for lowering a stimulation threshold of said skeletal muscle.

2. An apparatus according to claim 1 wherein said lowering means further comprises an anti-inflammatory drug.

3. An apparatus according to claim 2 wherein said anti-inflammatory drug further comprises a steroid.

4. An apparatus according to claim 3 wherein said steroid further comprises glucocorticosteroid.

5. An apparatus according to claim 1 or 2 or 3 or 12 wherein said holding means further comprises a shapened portion of said length of suture material.

6. An apparatus according to claim 5 wherein said shapened portion of said length of suture material further comprises a loosely wound helix.

* * * * *

UNITED STATES PATENT AND TRADEMARK OFFICE
CERTIFICATE OF CORRECTION

PATENT NO. : 5,009,229
DATED : April 23, 1991
INVENTOR(S) : Pierre-Andre Grandjean, and Philip H. J. Lee It is certified that error appears in the above-indentified patent and that said Letters Patent is hereby corrected as shown below:

Column 1, Line 27, delete "Khalafalle", and insert in its place --Khalafalla--.

Column 4, Line 56, delete "12", and insert in its place --4--.

Signed and Sealed this

Twenty-seventh Day of September, 1994

Attest:

BRUCE LEHMAN

Attesting Officer

Commissioner of Patents and Trademarks